United States Patent
Lin et al.

(10) Patent No.: US 7,569,722 B2
(45) Date of Patent: *Aug. 4, 2009

(54) PROCESS FOR REMOVAL OF BENZOIC ACID FROM AN OXIDIZER PURGE STREAM

(75) Inventors: Robert Lin, Kingsport, TN (US); Philip Edward Gibson, Kingsport, TN (US); Kenny Randolph Parker, Afton, TN (US)

(73) Assignee: Eastman Chemical Company, Kingsport, TN (US)

(*) Notice: Subject to any disclaimer, the term of this patent is extended or adjusted under 35 U.S.C. 154(b) by 707 days.

This patent is subject to a terminal disclaimer.

(21) Appl. No.: 11/201,799

(22) Filed: Aug. 11, 2005

(65) Prior Publication Data

US 2007/0038003 A1 Feb. 15, 2007

(51) Int. Cl.
C07C 51/00 (2006.01)
(52) U.S. Cl. .................. 562/414; 562/494; 203/15
(58) Field of Classification Search ........... 562/414, 562/494; 203/15
See application file for complete search history.

(56) References Cited

U.S. PATENT DOCUMENTS

| | | | |
|---|---|---|---|
| 2,964,559 A | 12/1960 | Burney et al. | |
| 3,840,641 A | 10/1974 | Wampflier et al. | |
| 3,873,468 A | 3/1975 | Kobinata et al. | |
| 3,950,409 A | 4/1976 | Yokota et al. | |
| 3,996,271 A | 12/1976 | Yokota et al. | |
| 4,081,464 A | 3/1978 | Marsh et al. | |
| 4,158,738 A | 6/1979 | Scott et al. | |
| 4,185,073 A | 1/1980 | Marsh et al. | |
| 4,219,669 A | 8/1980 | Tsuchiya et al. | |
| 4,298,580 A | 11/1981 | Harper et al. | |
| 4,330,676 A | 5/1982 | Moxham | |
| 4,356,319 A | 10/1982 | Roffia et al. | |
| 4,769,489 A | 9/1988 | Abrams et al. | |
| 4,892,972 A | 1/1990 | Schroeder et al. | |
| 4,914,230 A | 4/1990 | Abrams et al. | |
| 4,939,297 A | 7/1990 | Browder et al. | |
| 5,200,557 A | 4/1993 | Gee et al. | |
| 5,643,468 A | 7/1997 | Ure | |
| 5,676,847 A | 10/1997 | Yamamoto et al. | |
| 5,705,682 A | 1/1998 | Ohkoshi et al. | |
| 5,770,765 A | 6/1998 | Ohkoshi | |
| 5,840,965 A | 11/1998 | Turner et al. | |
| 5,916,422 A | 6/1999 | Kimura et al. | |
| 5,955,394 A | 9/1999 | Kelly | |
| 5,994,567 A | 11/1999 | Kingsley et al. | |
| 6,054,610 A | 4/2000 | Lee et al. | |
| 6,133,476 A | 10/2000 | Lin | |
| 6,153,790 A | 11/2000 | June et al. | |
| 6,562,997 B2 | 5/2003 | Sikkenga et al. | |
| 7,074,954 B2 | 7/2006 | Sheppard et al. | |
| 7,132,566 B2 | 11/2006 | Sumner et al. | |
| 7,273,559 B2 | 9/2007 | Gibson et al. | |
| 7,291,270 B2 | 11/2007 | Gibson et al. | |
| 7,402,694 B2 * | 7/2008 | Lin et al. | 562/414 |
| 2001/0041811 A1 | 11/2001 | Sikkenga et al. | |
| 2002/0016500 A1 | 2/2002 | Matsumoto et al. | |
| 2002/0193630 A1 | 12/2002 | Lin et al. | |
| 2004/0225148 A1 | 11/2004 | Isogai et al. | |
| 2004/0244536 A1 | 12/2004 | Lin | |
| 2004/0245176 A1 | 12/2004 | Parker et al. | |
| 2004/0249207 A1 | 12/2004 | Lin et al. | |
| 2004/0249208 A1 | 12/2004 | Lin et al. | |
| 2007/0205153 A1 | 9/2007 | Parker et al. | |
| 2007/0208195 A1 | 9/2007 | Gibson et al. | |
| 2007/0208196 A1 | 9/2007 | Parker et al. | |
| 2007/0208197 A1 | 9/2007 | Gibson et al. | |
| 2007/0208198 A1 | 9/2007 | Parker et al. | |
| 2007/0208199 A1 | 9/2007 | Parker et al. | |
| 2007/0213557 A1 | 9/2007 | Seiki et al. | |
| 2008/0103333 A1 | 5/2008 | Nubel et al. | |

FOREIGN PATENT DOCUMENTS

| | | |
|---|---|---|
| DE | 2131470 A | 6/1970 |
| EP | 0 181 127 A2 | 5/1986 |
| EP | 0 764 627 A1 | 3/1997 |
| EP | 0 579 715 B1 | 8/1997 |
| EP | 1 484 305 A1 | 8/2004 |
| EP | 1 484 306 A1 | 8/2004 |
| GB | 892766 | 3/1962 |
| GB | 1407705 | 9/1975 |
| GB | 2067563 | 7/1981 |
| JP | 46-14339 B | 11/1974 |
| JP | 51-145488 A | 12/1976 |
| JP | 49-123191 A | 2/1979 |
| JP | 54-25292 A | 2/1979 |
| JP | 62-25651 B2 | 6/1987 |
| JP | 09-048744 A | 2/1997 |

(Continued)

OTHER PUBLICATIONS

Notice of Allowance dated Aug. 1, 2007 for copending U.S. Appl. No. 10/975,252.
Notice of Allowance dated Jul. 18, 2007 for copending U.S. Appl. No. 10/975,256.
Copending U.S. Appl. No. 11/839,575, filed Aug. 16, 2007, Philip Edward Gibson et al.
Copending U.S. Appl. No. 11/839,578, filed Aug. 16, 2007, Philip Edward Gibson et al.
Copending U.S. Appl. No. 11/839,582, filed Aug. 16, 2007, Philip Edward Gibson et al.
Copending U.S. Appl. No. 11/839,573, filed Aug. 16, 2007, Kenny Randolph Parker et al.

(Continued)

*Primary Examiner*—Steven Bos
(74) *Attorney, Agent, or Firm*—Steven A. Owen; Bernard J. Graves, Jr.

(57) ABSTRACT

A process is disclosed that relates to the removal of impurities, specifically benzoic acid, from a mother liquor produced in the synthesis of carboxylic acid, typically terephthalic acid.

16 Claims, 5 Drawing Sheets

FOREIGN PATENT DOCUMENTS

| | | |
|---|---|---|
| JP | 9-157214 A | 6/1997 |
| JP | 10-114699 A | 5/1998 |
| JP | 11-349529 A | 12/1999 |
| JP | 3211396 B2 | 9/2001 |
| JP | 3232678 B2 | 11/2001 |
| JP | 59-53441 A | 3/2004 |
| KR | 1991-5989 B1 | 8/1991 |
| WO | WO 92/18453 | 10/1992 |
| WO | WO 92/18454 A1 | 10/1992 |
| WO | WO 93/24441 A | 12/1993 |
| WO | WO 97/27168 | 7/1997 |
| WO | WO 97/30963 A | 8/1997 |
| WO | WO 00/31014 A1 | 6/2000 |
| WO | WO 01/55075 A2 | 8/2001 |

OTHER PUBLICATIONS

Copending U.S. Appl. No. 11/842,413, filed Aug. 21, 2007, Kenny Randolph Parker et al.
USPTO Office Action dated Mar. 14, 2008 for copending U.S. Appl. No. 10/948,678.
USPTO Office Action dated Mar. 11, 2008 for copending U.S. Appl. No. 11/655,395.
USPTO Office Action dated Mar. 11, 2008 for copending U.S. Appl. No. 11/839,582.
USPTO Office Action dated Mar. 11, 2008 for copending U.S. Appl. No. 11/839,573.
Copending U.S. Appl. No. 12/050,251, filed Mar. 18, 2008, Robert Lin et al.
Copending U.S. Appl. No. 12/050,253, filed Mar. 18, 2008, Robert Lin et al.
Copending U.S. Appl. No. 12/050,256, filed Mar. 18, 2008, Robert Lin et al.
Copending U.S. Appl. No. 12/050,258, filed Mar. 18, 2008, Robert Lin et al.
USPTO Office Action dated Sep. 25, 2007 for copending U.S. Appl. No. 11/655,396.
USPTO Office Action dated Sep. 25, 2007 for copending U.S. Appl. No. 11/655,395.
USPTO Office Action dated Jul. 6, 2007 for copending U.S. Appl. No. 10/455,016.
USPTO Office Action dated May 11, 2007 for copending U.S. Appl. No. 10/455,017.
USPTO Office Action dated May 14, 2007 for copending U.S. Appl. No. 10/455,018.
USPTO office action dated Nov. 30, 2006 for copending U.S. Appl. No. 10/975,256.
USPTO office action dated Nov. 30, 2006 for copending U.S. Appl. No. 10/975,252.
USPTO office action dated Jan. 18, 2007 for copending U.S. Appl. No. 10/455,017.
USPTO office action dated Jul. 19, 2006 for copending U.S. Appl. No. 10/455,017.
USPTO office action dated Jul. 19, 2006 for copending U.S. Appl. No. 10/455,018.
USPTO office action dated Jul. 19, 2006 for copending U.S. Appl. No. 10/455,016.
Treybal, Robert E., "Stagewise Contact, Single-Stage Extraction," Mass-Transfer Operations, Third Edition, 1980, pp. 490-555, McGraw-Hill Book Company.
BHS—Werk Sonthofen, *BHS-FEST Pressure Filter*, 1990, pamphlet, Santhofen, West Germany.
USPTO Office Action dated Oct. 20, 2004 for U.S. Appl. No. 10/455,017.
USPTO Office Action dated Jun. 6, 2005 for U.S. Appl. No. 10/455,017.
USPTO Office Action dated Nov. 10, 2005 for U.S. Appl. No. 10/455,017.
Copending U.S. Appl. No. 10/156,312, filed May 28, 2002.
Copending U.S. Appl. No. 10/948,591, filed Sep. 24, 2004.
Copending U.S. Appl. No. 10/948,678, filed Sep. 24, 2004.
Copending U.S. Appl. No. 10/975,256, filed Oct. 28, 2004.
Copending U.S. Appl. No. 10/975,252, filed Oct. 28, 2004.
USPTO Office Action dated Apr. 4, 2008 for copending U.S. Appl. No. 11/181,449.
USPTO Notice of Allowance dated Jan. 15, 2008 for copending U.S. Appl. No. 10/544,016.
USPTO Office Action dated Feb. 14, 2008 for copending U.S. Appl. No. 11/842,469.
USPTO Office Action dated Mar. 4, 2008 for copending U.S. Appl. No. 11/839,575.
USPTO Office Action dated Mar. 5, 2008 for copending U.S. Appl. No. 11/655,317.
USPTO Office Action dated Mar. 4, 2008 for copending U.S. Appl. No. 11/839,578.
USPTO Office Action dated Mar. 5, 2008 for copending U.S. Appl. No. 11/655,396.
USPTO Office Action dated Mar. 7, 2008 for copending U.S. Appl. No. 10/948,591.
USPTO Office Action dated Apr. 25, 2008 for copending U.S. Appl. No. 11/181,214.
USPTO Office Action dated Sep. 11, 2007 for copending U.S. Appl. No. 10/455,017.
USPTO Notice of Allowance dated Sep. 11, 2007 for copending U.S. Appl. No. 10/455,018.
USPTO Notice of Allowance dated Oct. 1, 2008 for copending U.S. Appl. No. 10/948,591.
USPTO Notice of Allowance dated Oct. 10, 2008 for copending U.S. Appl. No. 11/842,469.
USPTO Office Action dated Oct. 16, 2007 for copending U.S. Appl. No. 11/655,317.
USPTO Notice of Allowance dated Dec. 3, 2007 for copending U.S. Appl. No. 10/455,017.
Copending U.S. Appl. No. 11/655,395, filed Jan. 19, 2007, Philip E. Gibson et al.
Copending U.S. Appl. No. 11/655,317, filed Jan. 19, 2007, Philip E. Gibson et al.
Copending U.S. Appl. No. 11/655,396, filed Jan. 19, 2007, Kenny R. Parker et al.
USPTO Office Action dated Mar. 14, 2007, for copending U.S. Appl. No. 10/455,016.
USPTO Office Action dated May 17, 2007 for copending U.S. Appl. No. 11/201,512.
USPTO Office Action dated Dec. 5, 2008 for copending U.S. Appl. No. 11/655,396.
USPTO Office Action dated Dec. 11, 2008 for copending U.S. Appl. No. 11/839,575.
USPTO Office Action dated Dec. 10, 2008 for copending U.S. Appl. No. 11/839,578.
USPTO Office Action dated Dec. 10, 2008 for copending U.S. Appl. No. 11/839,582.
USPTO Office Action dated Dec. 11, 2008 for copending U.S. Appl. No. 11/839,573.
USPTO Office Action dated Apr. 13, 2009 for copending U.S. Appl. No. 11/181,449
USPTO Office Action dated Mar. 12, 2009 for copending U.S. Appl. No. 12/050,256.
USPTO Office Action dated Mar. 13, 2009 for copending U.S. Appl. No. 12/050,253.
USPTO Office Action dated Oct. 28, 2008 for copending U.S. Appl. No. 11/181,449.
USPTO Office Action dated May 21, 2009 for copending U.S. Appl. No. 11/181,214.
USPTO Notice of Allowance dated May 22, 2009 for copending U.S. Appl. No. 12/050,251.
USPTO Notice of Allowance dated Nov. 12, 2008 for copending U.S. Appl. No. 10/948,678.
USPTO Office Action dated Nov. 14, 2008 for copending U.S. Appl. No. 11/655,317.
USPTO Office Action dated Mar. 6, 2009 for copending U.S. Appl. No. 11/655,395.

\* cited by examiner

PROCESS FOR REMOVAL OF BENZOIC ACID FROM AN OXIDIZER PURGE STREAM

FIELD OF INVENTION

This invention relates to the removal of impurities, specifically benzoic acid, from a mother liquor produced in the synthesis of carboxylic acid, typically terephthalic acid. This invention also relates to the removal of impurities, specifically benzoic acid, from a benzoic acid bearing stream produced in the synthesis of carboxylic acid.

BACKGROUND OF THE INVENTION

Terephthalic acid is commercially produced by oxidation of paraxylene in the presence of a catalyst, such as, for example, Co, Mn, Br and a solvent. Terephthalic acid used in the production of polyester fibers, films, and resins must be further treated to remove impurities formed as a result of the oxidation of paraxylene.

Terephthalic acid (TPA) is an intermediate in the production of polyesters for plastics and fiber applications. Commercial processes for the manufacture of TPA are often based on the heavy-metal catalyzed oxidation of p-xylene, generally with a bromide promoter in an acetic acid solvent. Due to the limited solubility of TPA in acetic acid under practical oxidation conditions, a slurry of TPA crystals is usually formed in the oxidation reactor. Typically, the TPA oxidizer slurry is withdrawn from the reactor, and TPA solids are separated from the oxidizer mother liquor using conventional solid-liquid separation techniques. The oxidizer mother liquor, which contains most of the catalyst and promoter used in the process, is recycled to the oxidation reactor. Aside from the catalyst and promoter, the oxidizer mother liquor stream also contains dissolved TPA and many by-products and impurities. These by-products and impurities arise partially from minor impurities present in the p-xylene feed stream. Other impurities arise due to the incomplete oxidation of p-xylene resulting in partially oxidized products. Still other by-products result from competing side reactions formed as a result of the oxidation of p-xylene to terephthalic acid.

The TPA solids undergo a solid-liquid separation wherein fresh solvent is utilitized to displace a major portion of the liquid component of the oxidizer mother liquor. After drying, the TPA solids are contaminated with impurities that were present in the oxidizer mother liquor since these impurities may be incorporated into the TPA solids. Impurities are also present due to occlusions in the TPA crystal structure and due to incomplete removal of the oxidizer mother liquor by the fresh solvent wash.

Many of the impurities in the oxidizer mother liquor stream that are recycled are relatively inert to further oxidation. Such impurities include, for example, isophthalic acid, phthalic acid and trimellitic acid. Impurities, which may undergo further oxidation are also present, such as, for example, 4-carboxybenzaldehyde, p-toluic acid and p-tolualdehyde. Oxidation inert impurities tend to accumulate in the oxidizer mother liquor upon recycle. The concentration of these inert impurities will increase in the oxidizer mother liquor until an equilibria is reached whereby the rate of removal of each impurity via the TPA product balances with the rate of formation and the rate of addition to the oxidation process. The normal level of impurities in commercial crude TPA makes it unsuitable for direct use in most polymer applications.

Conventionally, crude TPA has been purified either by conversion of a dimethyl ester or by dissolution in water with subsequent hydrogenation over standard hydrogenation catalysts. More recently, secondary oxidative treatments have been used to produce polymer-grade TPA. It is desirable to minimize the concentration of impurities in the mother liquor and thereby facilitate subsequent purification of TPA. In some cases, it is not possible to produce a purified, polymer-grade TPA unless some means for removing impurities from the oxidizer mother liquor stream are utilized.

One technique for impurity removal from a recycle stream commonly used in the chemical processing industry is to draw out or "purge" some portion of the recycle stream. Typically, the purge stream is simply disposed of or, if economically justified, subjected to various treatments to remove undesired impurities while recovering valuable components. One example of this process is U.S. Pat. No. 4,939,297 herein incorporated by reference in its entirety to the extent it does contradict statements herein. The amount of purge required for control of impurities is process-dependent; however, a purge amount equal to 10-40 wt % of the total oxidizer mother liquor stream is usually sufficient to produce TPA adequate as feedstock for commercial polymer manufacture. In the production of TPA, the percentage of the oxidizer mother liquor stream purge necessary to maintain acceptable impurity concentrations, coupled with the economic value of the metal catalyst and solvent components in the oxidizer purge stream, make simple disposal of the oxidizer purge stream economically unattractive. Thus, there is a need for a process that recovers essentially all of the valuable metal catalysts and acetic acid contained in the oxidizer purge stream while removing a major portion of the impurities present in the oxidizer purge stream. The metal catalyst can be recovered in an active form suitable for reuse by direct recycling to the p-xylene oxidation step.

One benefit of this invention is the energy and capital cost savings compared with the extraction based purge process previously described.

Another benefit of this invention is its efficacy compared with extraction purge processes regarding the usefulness of the solvent stream(s) recycled to the TPA process. The primary motivation in a liquid extraction process is based upon the assumption that introducing any aromatic impurities into a p-xylene oxidation process for producing terephthalic acid has a detrimental effect on the terephthalic acid powder quality (e.g. yellow color). Hence, it was assumed that a broad spectrum removal of aromatic impurities, such as provided by liquid extraction, was necessary to achieve appropriate terephthalic acid powder quality.

In one embodiment of this invention, however, employs a relatively simple process that separates benzoic acid from an aqueous solvent. The efficiency of the process toward benzoic acid is high since benzoic acid is more volatile (a higher vapor pressure) than most identified aromatic impurities in the production of a carboxylic acid, typically terephthalic acid. These aromatic impurities include, but are not limited to, trimellitic acid, isophthalic acid, stilbenes, and anthraquinones. Therefore, it is rather surprising that removal of a benzoic acid in favor of the other known impurities, that are inherently colored, would be sufficient to produce a carboxylic acid, typically terephthalic acid of good quality.

SUMMARY OF THE INVENTION

In a first embodiment of this invention, a process is provided. The process comprises:
(a) subjecting a benzoic acid bearing stream comprising water and benzoic acid to evaporation in a evaporator zone to form a solvent rich vapor and a wash filtrate residue; and (b) subjecting said solvent rich vapor to distillation in a separation zone to form a solvent rich stream and a benzoic acid rich stream; wherein said benzoic acid rich stream comprises at least 15% by weight benzoic acid.

In another embodiment of this invention, a process is provided. The process comprises:
(a) subjecting a benzoic acid bearing stream comprising water and benzoic acid to evaporation in a evaporator zone to form a solvent rich vapor and a wash filtrate residue; and
(b) subjecting said solvent rich vapor to distillation in a separation zone to form a solvent rich stream and a benzoic acid rich stream; wherein said benzoic acid rich stream comprises at least 15% by weight benzoic acid; and
(c) recycling at least a portion of the solvent rich stream back to an oxidation reactor in an aromatic oxidation process. In another embodiment of this invention, a process is provided. The process comprises:
(a) subjecting a benzoic acid bearing stream comprising water and benzoic acid to evaporation in a evaporator zone to form a solvent rich vapor and a wash filtrate residue; wherein said benzoic acid bearing stream is produced in an aromatic oxidation process;
(b) subjecting said solvent rich vapor to distillation in a separation zone to form a solvent rich stream and a benzoic acid rich stream; wherein said benzoic acid rich stream comprises at from about 5 wt % to about 35 wt % benzoic acid; and
(c) recycling at least 50 wt % of the solvent rich stream to an oxidation reactor in an aromatic oxidation process.

DESCRIPTION OF THE INVENTION

Figure 1:
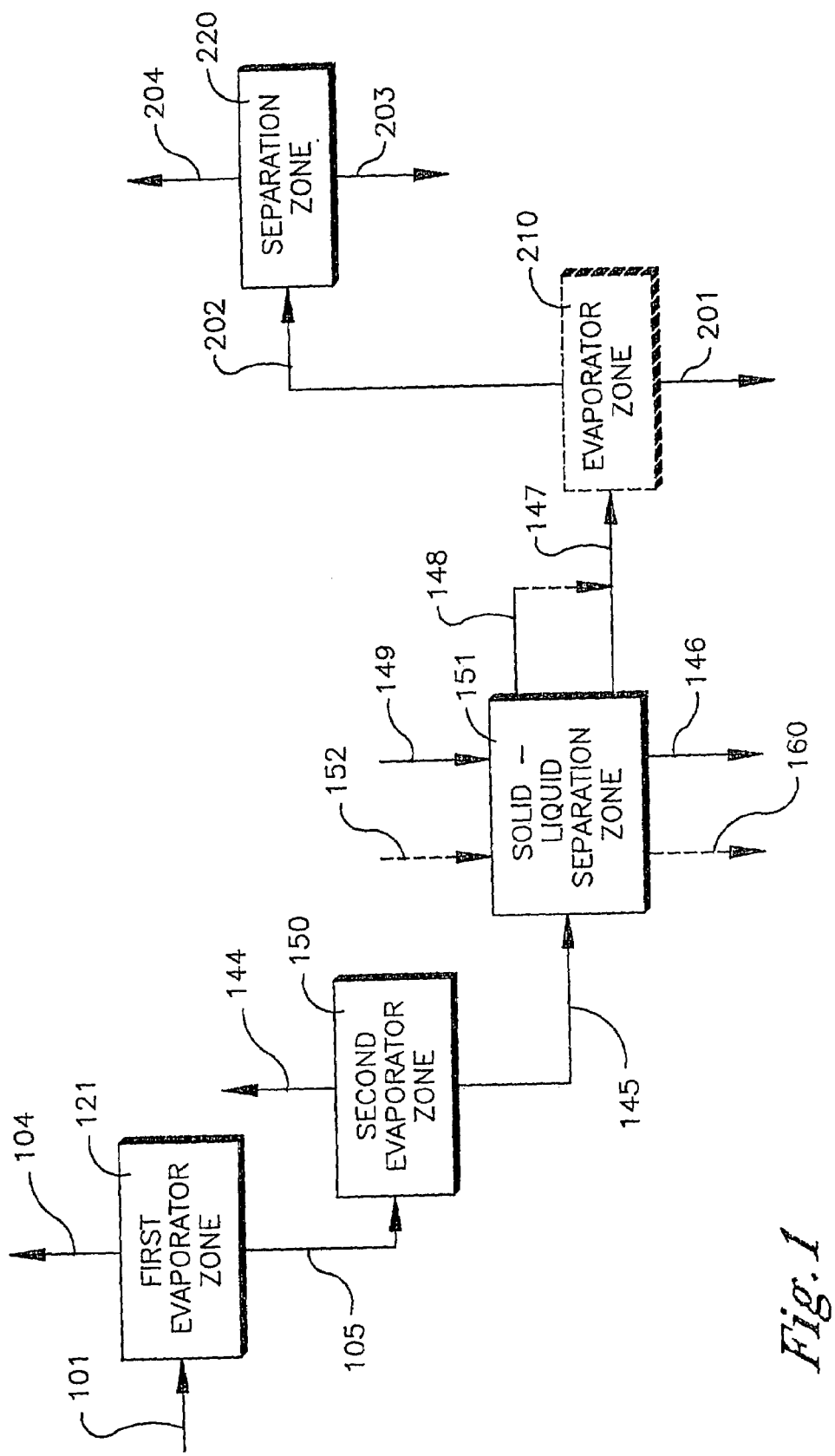
FIG. 1 illustrates different embodiments of the invention wherein a process to recover benzoic acid from an oxidizer purge stream 101 is shown.

In one embodiment of this invention, a process to separate benzoic acid from an oxidizer purge stream 101 is provided as shown in FIG. 1.

Step (a) comprises subjecting an oxidizer purge stream 101 to evaporation in a first evaporator zone 121 to produce a vapor stream 104 and a concentrated purge slurry 105.

In an embodiment of the invention, the oxidizer purge stream 101 is withdrawn from a carboxylic acid oxidative synthesis process. The oxidizer purge stream 101 serves as the feed stream to the present process. In an embodiment of the invention, the oxidizer purge stream 101 comprises at least one carboxylic acid, at least one solvent, at least one metal catalyst and impurities. The impurities comprise at least one impurity selected from the group consisting of organic bromides, corrosion metals, p-xylene oxidation by-products, and impurities derived as a result of impurities in the p-xylene. The organic bromides may be used as promoters in the oxidation reaction. Examples of corrosion metals are iron and chromium compounds, which inhibit, reduce or entirely destroy the activity of the metal catalyst. Aside from the catalyst and promoter, the oxidizer purge stream 101 also contains by-products and impurities. These by-products and impurities arise partially from minor impurities present in the p-xylene feed stream. Other impurities arise due to the incomplete oxidation of p-xylene resulting in partially oxidized products. Still other by-products result from competing side reactions in the oxidation of p-xylene to terephthalic acid.

The carboxylic acids include any aromatic carboxylic acids produced via controlled oxidation of an organic substrate. Such aromatic carboxylic acids include compounds with at least one carboxylic acid group attached to a carbon atom that is part of an aromatic ring, preferably having at least 6 carbon atoms, even more preferably having only carbon atoms. Suitable examples of such aromatic rings include, but are not limited to, benzene, biphenyl, terphenyl, naphthalene, and other carbon-based fused aromatic rings. Examples of suitable carboxylic acids include, but are not limited to, terephthalic acid, benzoic acid, p-toluic acid, isophthalic acid, trimellitic acid, naphthalene dicarboxylic acid, 2,5-diphenyl-terephthalic acid, and mixtures thereof.

Suitable solvents include, but are not limited to, aliphatic mono-carboxylic acids, preferably containing 2 to 6 carbon atoms, or benzoic acid and mixtures thereof and mixtures of these compounds with water. Preferably, the solvent is acetic acid mixed with water in a ratio of about 5:1 to about 25:1, preferably between about 8:1 and about 20:1. Throughout the specification, acetic acid will be referred to as the solvent. However, it should be appreciated that other suitable solvents, such as those disclosed previously, may also be utilized.

In the first step of the present process, the oxidizer purge stream 101 is concentrated by conventional means in a first evaporator zone 121 comprising at least one evaporator to produce a vapor stream 104 and a concentrated purge slurry 105. In an embodiment to the invention, the evaporator is operated at atmospheric or slightly super atmospheric conditions, generally from about 1 atmosphere to about 10 atmospheres. The vapor stream 104 comprises a majority of the water and solvent, and the concentrated purge slurry 105 comprises the remainder of the water and solvent not removed from the oxidizer purge stream 101. As used herein "majority" means greater than 50% by weight. In an embodiment of the invention, the evaporation removes about 50 wt % (weight percent) to about 80 wt % of the solvent and water, typically acetic acid and water, which are present in the oxidizer purge stream 101.

Step (b) comprising subjecting the concentrated purge slurry 105 to evaporation in a second evaporator zone 150 to produce a solvent rich stream 144 and a super concentrated purge slurry 145.

In an embodiment of the invention, the second evaporator zone 150 comprises at least one evaporator operated at vacuum conditions. In an embodiment of the invention, the evaporation can be conducted at a temperature from about 20° C. to about 70° C.; another range is from about 30° C. to about 50° C. In an embodiment of the invention, the combination of evaporators 121 and 150 is operated so as to concentrate the oxidizer purge stream as represented by stream 101 to a condition wherein about 75 wt % to about 99 wt % of the solvent and water, typically acetic acid and water, are removed from the oxidizer purge stream 101 to produce the super concentrated purge slurry 145. In another embodiment of the invention another range for operation of the combination of evaporators 121 and 150 is operated so as to concentrate the oxidizer purge stream as represented by stream 101 to a condition wherein about 85 wt % to about 99 wt % of the solvent and water, typically acetic acid and water, is removed from the oxidizer purge stream 101 to produce the super concentrated purge slurry 145.

Figure 4:
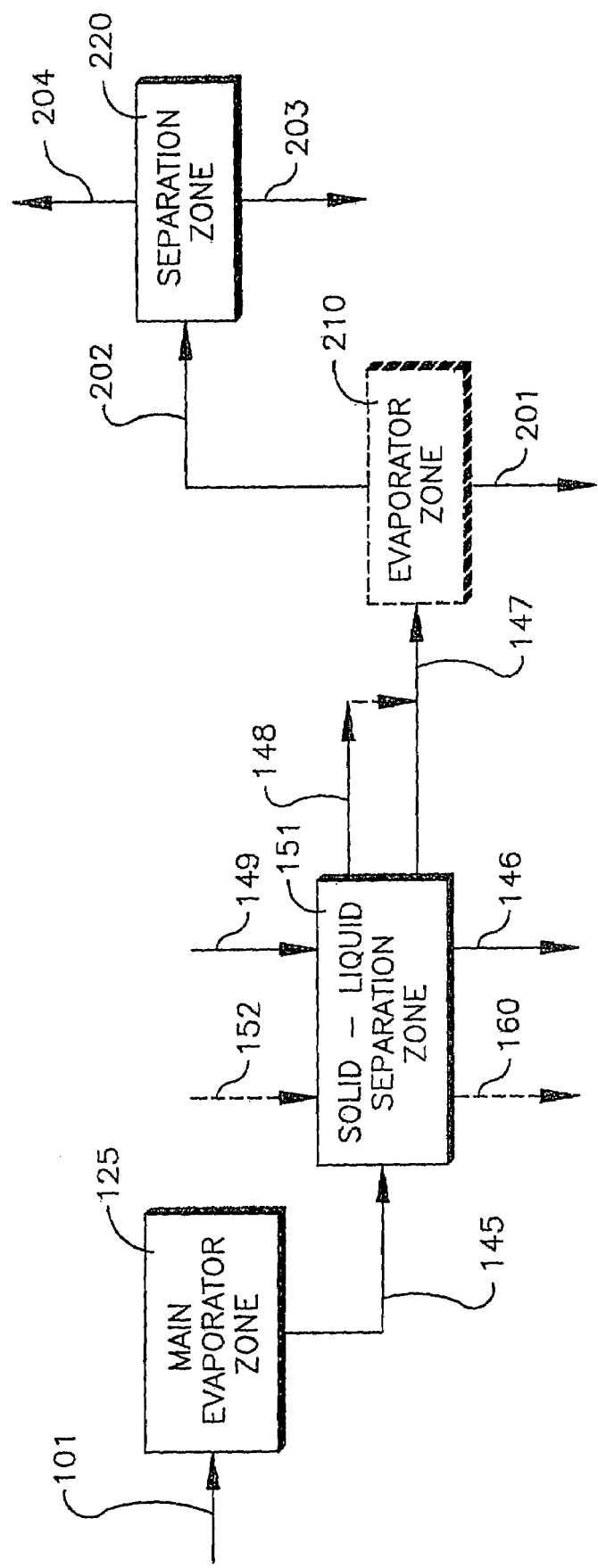
FIG. 4 illustrates an embodiment of the invention wherein a process to recover benzoic acid from an oxidizer purge stream 101 is shown, and the process utilizes a main evaporator zone 125.

In another embodiment of the invention, the first evaporation zone 121 and the second evaporator zone can be combined in a main evaporation zone 125 as shown in FIG. 4. The main evaporation zone 125 comprises at least one evaporator. The evaporator or evaporators in the main evaporation zone 125 are operated at a temperature and pressure sufficient to remove at least 75% by weight of the solvent and water combined from the oxidizer purge stream 101. In another embodiment of the invention, the evaporator or evaporators in the main evaporation zone 125 are operated at a temperature and pressure sufficient to remove at least 85% by weight of the solvent and water combined from the oxidizer purge stream. In another embodiment of the invention, the evaporator or evaporators in the main evaporation zone 125 are operated at a temperature and pressure sufficient to remove at least 90% by weight of the solvent and water combined from the oxidizer purge stream 101. In another embodiment of the invention, the evaporator or evaporators in the main evaporation zone 125 are operated at a temperature and pressure sufficient to remove at least 95% by weight of the solvent and water combined from the oxidizer purge stream.

Ranges stated in this disclosure and the claims that follow should be understood to disclose the entire range specifically and not just the end point(s). For example, disclosure of the range 0 to 10 should be taken to specifically disclose 2, 2.5, 3.17 and all other number subsumed and not just 0 and 10.

In an embodiment of the invention, the condition of the super concentrated purge slurry 145 can be as a solid-liquid mixture with only enough solvent to provide pumpability.

Step (c) comprises filtering the super concentrated purge slurry 145 in a solid-liquid separation zone 151 to form a filter cake 154 and a mother liquor 147.

Step (d) comprises washing the filter cake 154 with a wash feed 149 in the solid-liquid separation zone 151 to form a washed cake 146 and a wash filtrate 148; and optionally dewatering the washed cake 146 in the solid-liquid separation zone 151 to form a dewatered cake 159; wherein the solid-liquid separation zone 151 comprises at least one pressure filtration device.

Figure 2:
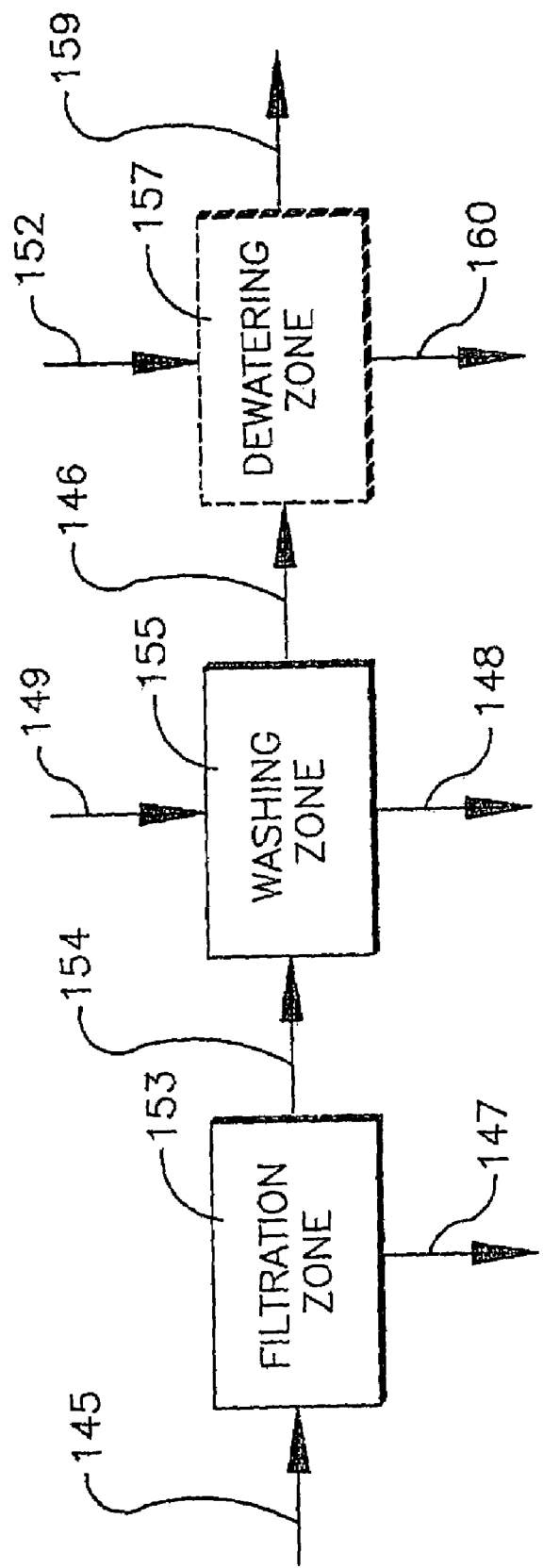
FIG. 2 illustrates an embodiment of the process occurring in the solid-liquid separation zone 151 wherein the solid-liquid separation zone comprises a filtration zone 153, a washing zone 155, and optionally a dewatering zone 157.

In an embodiment of the invention, the super concentrated purge slurry 145 is introduced in the solid-liquid separation zone 151 where the solid-liquid separation zone comprises a filtration zone 153, a washing zone 155, and optionally a drying zone 157 as shown in FIG. 2. The filtration zone 153 comprises a filter cell, or a series of filter cells, physically situated to permit a filter cake 154 to develop a distribution across the area of the filter cell to hinder or prevent the channeling of wash feed 149 through the filter cake 154.

Suitably, a filter cake 154 of at least 0.25 inch in depth to about 8 inches in depth, preferably at least 0.5 inch in depth, more preferably at least 1 inch in depth, and even more preferably about 2 to about 4 inches in depth is distributed over the area of the filter cell. The washed cake, 146, can be recovered or further treated, recycled and/or sent to waste treatment facilities.

Upon obtaining a suitable or preferred height of filter cake 154 the filter cake 154 leaves the filtration zone 153 which comprises a filter or series of filters and enters a washing zone 155 where the filter cake 154 is contacted with a wash feed 149. In one embodiment of the invention, there is sufficient pressure across the filter cake 154 to allow a reservoir or buildup of the wash feed 149 over the filter cake 154 to a suitable depth, preferably to a minimum depth of 0.25 inch. A pressure gradient of at least 0.5 psi, preferably from about 5 psi to about 65 psi, across the filter cake 154 and the reservoir of wash feed 149 can be applied to displace any solute in the filter cake 154 with wash feed 149.

A filter cake 154 depth of at least 0.5 inch is suitable to obtain a filter cake 154 of sufficient compactness to furnish a wash vehicle, i.e. the filter cake 154, from which a wash filtrate 148 containing a solute from the filter cake 154 can be removed efficiently by displacement washing. If the filter cake depth 154 is less than about 0.25 inch, channeling of wash feed 149 in the filter cake 154 can occur resulting in non-uniform washing of the filter cake 154.

Because of the loss of efficiency in displacement washing of the filter cake 154, a minimum filter cake 154 depth of at least 0.25 inch of purified terephthalic acid is preferred.

A minimum liquid height above the filter cake 154 surface is required to ensure that displacement washing occurs. This height must be sufficient to ensure that the filter cake 154 surface is completely covered with wash feed 149. If the filter cake 154 surface is not covered with wash feed 149, bypassing of the wash feed 149 can occur without adequate displacement of the solute in the filter cake 154. Because of irregularities in the filter cake 154 surface, a minimum liquid height of about 0.25 inch is preferred above the filter cake 154 surface.

It has been found that displacement of the solute from the filter cake 154 using the wash feed 149 at high pressure permits an efficient separation of catalyst metals from the filter cake 154. Another benefit of high pressure is the reduction of wash feed 149 required to recover cobalt as shown in the examples.

Utilization of added stages in the solid-liquid separation zone 151 can decrease the amount of wash feed 149 required to reduce the total amount of metal catalyst retained in the filter cake 154. It is convenient therefore that a suitable number of stages of positive displacement washing be used to minimize total wash feed 149 used in displacement washing to reduce need for downstream waste treatment facilities.

It is understood that multiple stages of the displacement washing procedure can replace a single stage displacement washing procedure wherein the quantity of wash feed 149 is sufficient to obtain at least 80 wt % recovery of the metal catalyst from the super concentrated slurry 145 to the mother liquor 147 and the wash filtrate 148. Additionally, a procedure utilizing multiple stages of counter-current washing can be useful if reduction of the amount of wash feed 149 is determined to be advantageous.

In the process of the instant invention, a super concentrated purge slurry 145 is introduced into one or more of a series of filter cells physically situated to permit a filter cake 154 of requisite thickness to develop. Upon obtaining a minimum height of filter cake 154, about 0.25 to about 4 inches, the filter cake 154 leaves the filter or series of filters and enters a washing zone 155 where the filter cake 154 is washed with a wash feed 149. Pressure can then be applied to the wash feed 149 to displace the solute (i.e. the liquid and any dissolved compounds such as metal catalyst in the filter cake) of the filter cake 154. Upon displacement of the solute with the wash feed, the filter cake 154 can be discharged from the filtration zone 155 by any suitable means, and the cycle repeated. In an embodiment of the invention, the ratio of wash feed 149 to filter cake 154 discharge is within the range of from about 1:20 to about 20:1 to reduce the level of metal catalyst in the filter cake by greater than 95 wt %.

Equipment for performing the requisite washing cycle can comprise a series of filter cells maintained in a suitable position to permit a wash feed 149 reservoir to develop over the filter cells. In one embodiment of the invention, suitable equipment can comprise a rotary drum pressure filter with multiple filter cells, fitted with a means for discharging washed cake 146 from the filter cells. The filter cake 154 can be washed for as many times as required to develop a minimum concentration of metal catalyst in the washed cake 146 before discharging the washed cake 146 from the filter device.

A suitable pressure filter which can be adapted to the requirements of the instant invented process is a BHS-FEST™ rotary drum pressure filter, BHS-WERK, Sonthofen, D-8972, Sonthofen, West Germany, although other pressure filters which can accomplish the required operation can be used. Examples of other devices that can be used in the solid-liquid separation zone include 151, but are not limited to, pressure belt filters, filter presses, centrifuges, pressure leaf filters, and cross-flow filters. The pressure filter can be operated at a temperature and pressure sufficient to obtain at least 80 wt % recovery of the metal catalyst from the solute of the mother liquor 147. Preferably, the pressure filter can be operated at a temperature of about 25° C. to about 160° C., and a pressure of 1 atmospheres to 50 atmospheres.

In the operation of the BHS-FEST™ filter, a rotary drum contains a series of filter cells located on the periphery of the rotating drum. As the drum rotates, the filter cells receive a super concentrated purge slurry 145 and a filter cake 154 builds to a requisite depth. The mother liquor 147 is produced by filtration of the super concentrated purge slurry 145. Upon rotation of the drum, the filter cake 154 enters a washing zone 155 where a reservoir of wash feed 149 is built up over the filter cake 154 to a required depth. The applied pressure to the wash feed reservoir forces the water through the filter cake 154 to displace the solute (with dissolved metal catalyst) retained in the super concentrated purge slurry 145 to produce a washed cake 146. Upon further rotation of the drum, the wash cycle can be repeated at least three more times if necessary in a counter current fashion, after which the system pressure is released with attendant temperature decrease to ambient conditions. Optionally, the washed cake 146 can be dewatered in a dewatering zone 157 with a vapor via conduit 152 to produce a dewatered cake 159 and a humid vapor 160. The resultant dewatered cake 159 can then be discharged from the drum by any conventional means.

Figure 3:
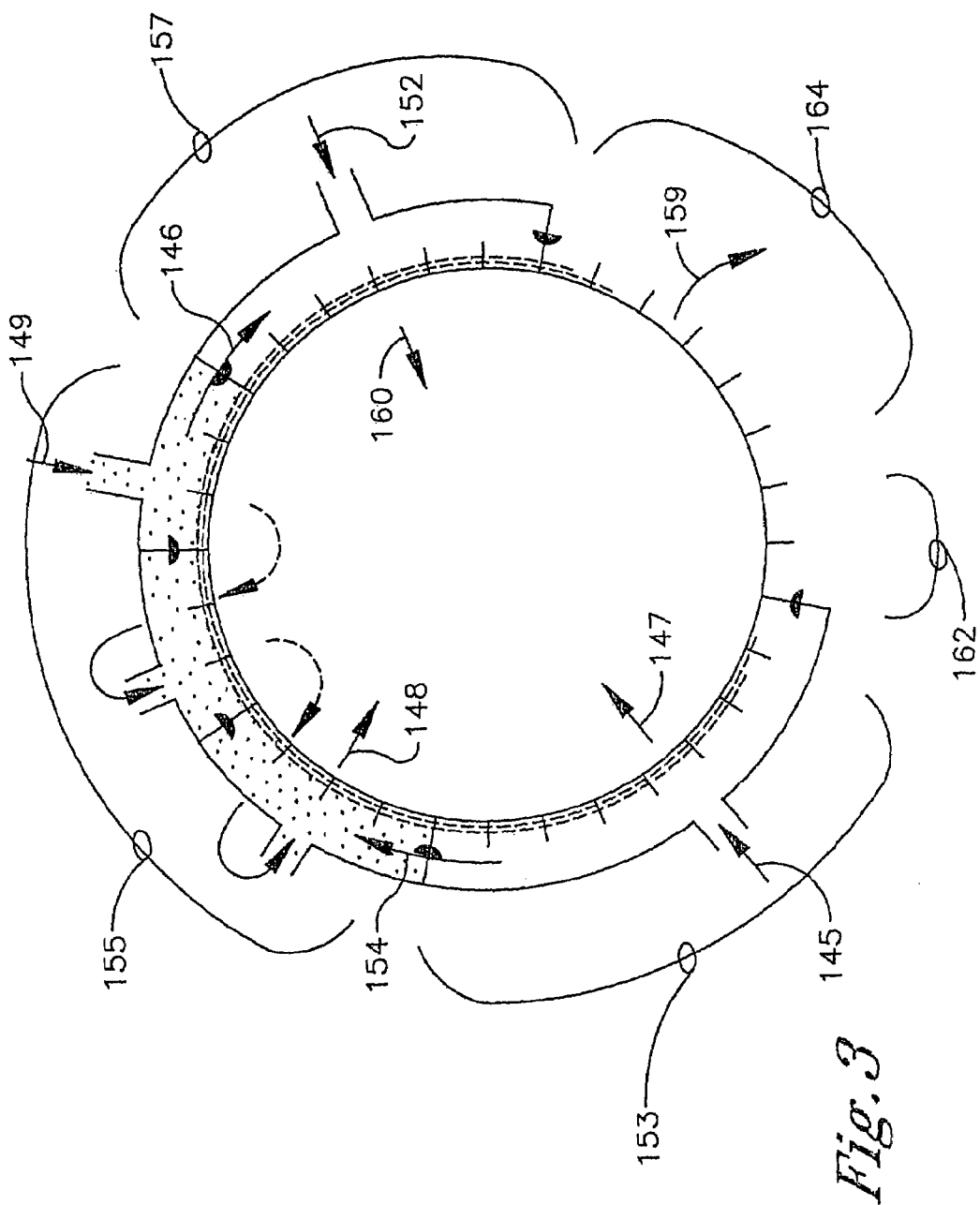
FIG. 3 illustrates an embodiment of the invention where a rotary pressure drum filter is utilized in the solid-liquid separation zone.

FIG. 3 illustrates an embodiment of the invention where a rotary pressure drum filter is utilized as the process filtration device. In an embodiment of the invention, the rotary drum pressure filter comprises a filtration zone 153, a wash zone 155, optionally, a dewatering zone 157, a discharge zone 164 and a cloth wash zone 162. The cloth wash zone shown in FIG. 3 is an embodiment of the invention where the rotary pressure drum filter comprises a cloth wash zone 162 where the filters are washed after discharge of the dewatered cake 159.

The wash filtrate 148 is produced by displacement washing the filter cake with the wash feed 149. The filter cake 154 within the solid-liquid separation zone 151 undergoes extraction of metal catalyst by introduction of the wash feed 149 to form the wash filtrate 148. In an embodiment of the invention, at least 80 wt % of the metal catalyst is recovered in the wash filtrate 148 and the mother liquor 147. In an embodiment of the invention, at least 90 wt % of the metal catalyst is recovered in the wash filtrate 148 and the mother liquor 147. The wash feed 149 comprises water and optionally an additional oxidation solvent.

Perhaps most surprisingly by utilizing water as a wash feed 149 at temperatures in the range of about 20° C. to about 70° C., preferably about 30° C. to about 50° C., sufficient corrosion metal is retained in the dewatered cake 159 wherein the need for corrosion metal removal by other means is eliminated. The dewatered cake 159 which represents solids stripped of metal catalyst can be disposed from the system.

Step (e) optionally comprises subjecting the mother liquor 147 and optionally the wash filtrate 148 to evaporation in an evaporator zone 210 to produce a solvent rich vapor stream 202 and wash filtrate residue 201.

The evaporator zone 210 comprises at least one evaporator. In an embodiment of the invention, the evaporator is operated at atmospheric or slightly super atmospheric conditions, generally from about 1 atmosphere to about 10 atmospheres. The solvent rich vapor 202 comprises a majority of the water and solvent, and the wash filtrate residue 201 comprises the remainder of the water and solvent not removed from the mother liquor 147 and the majority of the catalyst. The evaporation removes about 90 wt % to about 99 wt % of the solvent and water from the combined stream in conduit 147, typically acetic acid and water, which are present in the wash filtrate 148 and the majority of the benzoic acid in the mother liquor 147. "Majority" as used herein means greater than 50% by weight.

Step (f) comprises subjecting the solvent rich vapor stream 202 to conventional distillation in distillation zone 220 to form a benzoic acid rich stream 203 and a solvent rich stream 204.

The separation zone 220 comprises at least one liquid-vapor separator. In an embodiment of the invention, the separator operates at atmospheric or slightly super atmospheric conditions, generally from about 1 atmosphere to about 10 atmospheres. The liquid-vapor separator comprises at least one theoretical vapor-liquid equilibrium stage. Examples of liquid-vapor separators include, but are not limited to, flash condensers and distillation columns. In an embodiment of the invention, the benzoic rich acid stream 203 has greater than 5 wt % benzoic acid. In another embodiment of the invention, the benzoic acid rich stream 203 has greater than 15 wt % benzoic acid. In another embodiment of the invention, the benzoic acid rich stream 203 has greater than 30 wt % benzoic acid. In another embodiment of the invention, the benzoic acid rich stream 203 has greater than 50 wt % benzoic acid. In another embodiment of the invention, the benzoic acid rich stream 203 comprises from about 5 wt % to 75 wt % benzoic acid. In another embodiment of the invention, the benzoic acid rich stream 203 comprises from about 5 wt % to 50 wt % benzoic acid. In another embodiment of the invention, the benzoic acid rich stream 203 comprises from about 5 wt % to 35 wt % benzoic acid. In another embodiment of the invention, the benzoic acid rich stream 203 comprises from about 15 wt % to 30 wt % benzoic acid.

Step (g) comprises optionally recycling at least a portion of the solvent rich stream 204 back to an oxidation reactor in an aromatic oxidation process.

At least a portion of the solvent rich stream can be recycled back to an oxidation reactor in the oxidation process. "At least a portion" can mean at least 5 wt %, at least 15 wt %, at least 30 wt %, at least 50 wt %, at least 75 wt %, or all of the solvent rich stream is recycled 204 back to an oxidation reactor.

An example of an aromatic oxidation process is disclosed U.S. patent application Ser. No. 10/156,312 herein incorporated by reference in its entirety to the extent it does not contradict statements made herein.

Although the composition of the various streams in the process varies depending on the process conditions, a typical composition of the streams, using a computer simulated model (ASPEN version 12.1) of the process, are shown in Tables 1a and 1b. In Tables 1a and 1b, the components are shown in the left hand column, and the amount of these components in each stream in FIG. 1 are shown in the number column corresponding to the number of the stream in FIG. 1.

Figure 5:
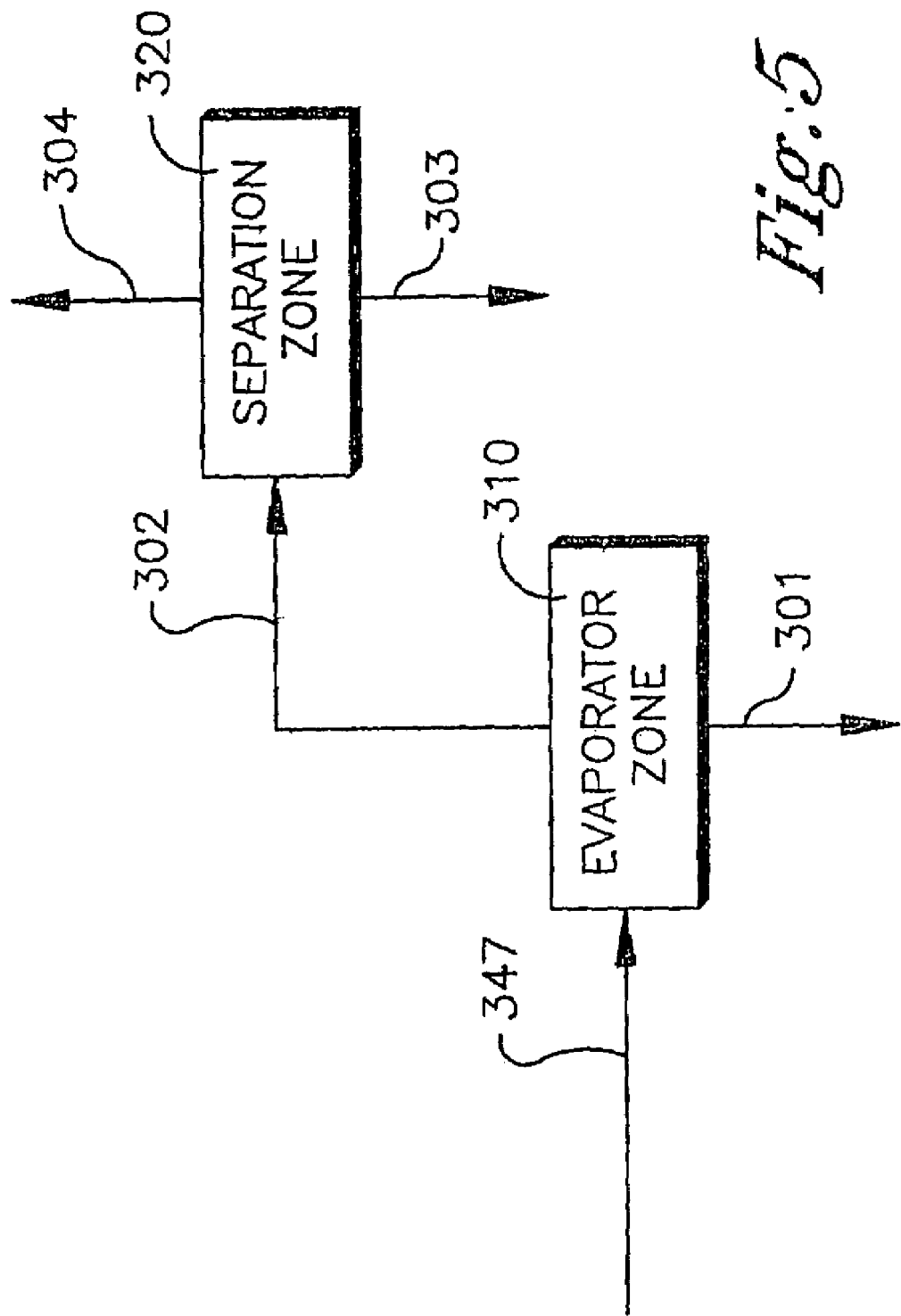
FIG. 5 illustrates an embodiment of the invention wherein a process to recovery benzoic acid from a benzoic acid bearing stream 347 is provided.

In another embodiment of the invention, a process is provided as shown in FIG. 5.

Step (a) optionally comprises subjecting a benzoic acid bearing stream 347 to evaporation in an evaporator zone 310 to produce a solvent rich vapor 302 and wash filtrate residue 301

The evaporator zone 310 comprises at least one evaporator. The benzoic acid bearing stream 347 comprises water and benzoic acid. In an embodiment of the invention, the evaporator is operated at atmospheric or slightly super atmospheric conditions, generally from about 1 atmosphere to about 10 atmospheres. The solvent rich vapor 302 comprises a majority of the water and solvent, and the wash filtrate residue 301 comprises the remainder of the water and solvent not removed from the benzoic acid bearing stream 347. In another embodiment of the invention, the evaporation removes about 90 wt % to about 99 wt % of the solvent and water from the benzoic acid bearing stream 347, typically acetic acid and water.

The benzoic acid bearing stream can be any stream produced in an aromatic oxidation process. An example of an aromatic oxidation process is disclosed in U.S. patent application Ser. No. 10/156,312 herein incorporated by reference in its entirety to the extent it does not contradict statements made herein.

For example, during the course of the oxidation reaction, exothermic heat of reaction and water generated by the oxidation of the dialkyl aromatic compound are removed from the reactor through the vaporization of a portion of the liquid reaction medium. These vapors, known as reactor offgas, comprise the aqueous solvent having five to thirty weight percent water and oxygen-depleted process gas containing minor amounts of decomposition products including catalyst residue. The reactor offgas can be used as the benzoic acid bearing stream.

In an embodiment of the invention, the evaporator zone, 310, is operated at atmospheric or slightly super atmospheric conditions, generally from about 1 atmosphere to about 10 atmospheres. The solvent rich vapor stream, 302, comprises benzoic acid, and the wash filtrate residue, 301, comprises solids not captured in the solid-liquid separation zone, including any residual catalyst metals.

Step (b) comprises subjecting the solvent rich vapor stream 302 to conventional distillation in seperation zone 320 to form a benzoic acid rich stream 303 and a solvent rich stream 304.

The separation zone 320 comprises at least one liquid-vapor separator. In an embodiment of the invention, the liquid vapor separator operates at atmospheric or slightly super atmospheric conditions, generally from about 1 atmosphere to about 10 atmospheres. The liquid-vapor separator comprises at least one theoretical vapor-liquid equilibrium stage. Examples of liquid-vapor separators include, but are not limited to, flash condensers and distillation columns.

In an embodiment of the invention, the benzoic rich acid stream 303 has greater than 5 wt % benzoic acid. In another embodiment of the invention, the benzoic acid stream has greater than 15 wt % benzoic acid.

In another embodiment of the invention, the benzoic acid rich stream 303 has greater than 30 wt % benzoic acid. In another embodiment of the invention the benzoic acid rich stream 303 has greater than 50 wt % benzoic acid. In another embodiment of the invention, the benzoic acid rich stream 303 comprises from about 5 wt % to 75 wt % benzoic acid. In another embodiment of the invention, the benzoic acid rich stream 303 comprises from about 5 wt % to 50 wt % benzoic acid. In another embodiment of the invention, the benzoic acid rich stream 303 comprises from about 5 wt % to 35 wt % benzoic acid. In another embodiment of the invention, the benzoic acid rich stream 303 comprises from about 15 wt % to 30 wt % benzoic acid.

Step (c) comprises optionally recycling at least a portion of the solvent rich stream 304 back to an oxidation reactor in an aromatic oxidation process.

At least a potion of the solvent rich stream can be recycled to an oxidation reactor in the oxidation process. At least a portion can mean at least 5, at least 15 wt %, at least 30 wt %, at least 50 wt %, at least 75 wt % or all of the solvent rich stream is recycled 304 to an oxidation reactor.

TABLE 1A

ASPEN SIMULATION OF PROCESS

| | 101 MASS % | 104 MASS % | 105 MASS % | 144 MASS % | 145 MASS % | 146 MASS % | 147 MASS % |
|---|---|---|---|---|---|---|---|
| WATER | 7.7 | 8.9 | 4.5 | 6.0 | 2.7 | 20.0 | 3.5 |
| ACETIC ACID | 88.4 | 91.1 | 80.2 | 94.0 | 66.7 | 0.0 | 86.6 |
| TEREPTHALIC ACID | 2.9 | 0.0 | 11.4 | 0.0 | 22.7 | 74.0 | 2.3 |
| OTHER ORGANICS | 0.6 | 0.1 | 2.0 | 0.0 | 4.0 | 5.9 | 3.1 |
| BENZOIC ACID | 0.3 | 0.0 | 1.1 | 0.0 | 2.1 | 0.0 | 2.8 |
| METALS AND BROMINE COMPLEX | 0.2 | 0.0 | 0.9 | 0.0 | 1.8 | 0.1 | 1.7 |
| TOTAL FLOW kg/hr | 10000 | 7500 | 2500 | 1241 | 1259 | 351 | 894 |
| TEMPERATURE C. | 121.2 | 125.5 | 125.5 | 49.4 | 49.4 | 83.0 | 49.4 |

TABLE 1B

| | 148 MASS % | 149 MASS % | 201 MASS % | 202 MASS % | 203 MASS % | 204 MASS % |
|---|---|---|---|---|---|---|
| WATER | 89.8 | 100.0 | 0.0 | 3.7 | 1.2 | 3.9 |
| ACETIC ACID | 8.1 | 0.0 | 1.7 | 91.7 | 47.0 | 94.4 |
| TEREPHTHALIC ACID | 0.7 | 0.0 | 40.2 | 0.0 | 0.0 | 0.0 |
| OTHER ORGANICS | 0.3 | 0.0 | 27.1 | 1.6 | 20.3 | 0.5 |
| BENZOIC ACID | 0.3 | 0.0 | 0.7 | 2.9 | 31.5 | 1.2 |
| METALS AND BROMINE COMPLEX | 0.9 | 0.0 | 30.2 | 0.0 | 0.1 | 0.0 |
| TOTAL FLOW kg/hr | 801 | 787 | 51 | 845 | 48 | 795 |
| TEMPERATURE C. | 60.0 | 70.9 | 272.1 | 272.1 | 159.5 | 159.5 |

We claim:

1. A process comprising:
   (a) subjecting a benzoic acid bearing stream comprising water and benzoic acid to evaporation in an evaporator zone to form a solvent rich vapor and a wash filtrate residue; and
   (b) subjecting said solvent rich vapor to distillation in a separation zone to form a solvent rich stream and a benzoic acid rich stream;
   wherein said benzoic acid rich stream comprises at least 15% by weight benzoic acid.

2. The process according to claim 1 wherein said benzoic acid rich stream comprises benzoic acid in an amount greater than 30% by weight.

3. The process according to claim 1 wherein said benzoic acid bearing stream is produced in an aromatic oxidation process.

4. The process according to claim 1 wherein said benzoic acid bearing stream is a vapor stream produced in the oxidation of an aromatic compound.

5. The process according to claim 1 wherein said evaporator zone is operated between about 1 to about 10 atmospheres.

6. A process comprising:
   (a) subjecting a benzoic acid bearing stream comprising water and benzoic acid to evaporation in an evaporator zone to form a solvent rich vapor and a wash filtrate residue; and
   (b) subjecting said solvent rich vapor to distillation in a separation zone to form a solvent rich stream and a benzoic acid rich stream;
   wherein said benzoic acid rich stream comprises at least 15% by weight benzoic acid; and
   (c) recycling at least a portion of the solvent rich stream back to an oxidation reactor in an aromatic oxidation process.

7. The process according to claim 6 wherein said benzoic acid rich stream comprises benzoic acid in an amount greater than 30% by weight.

8. The process according to claim 6 wherein said benzoic acid bearing stream is produced in an aromatic oxidation process.

9. The process according to claim 6 wherein said benzoic acid bearing stream is a vapor stream produced in the oxidation of an aromatic compound.

10. The process according to claim 6 wherein at least 50 wt % of said benzoic acid rich stream is recycled to an oxidation reactor in an aromatic oxidation process.

11. The process according to claim 6 wherein said evaporator zone is operated between about 1 to about 10 atmospheres.

12. A process comprising:
    (a) subjecting a benzoic acid bearing stream comprising water and benzoic acid to evaporation in an evaporator zone to form a solvent rich vapor and a wash filtrate residue; wherein said benzoic acid bearing stream is produced in an aromatic oxidation process;
    (b) subjecting said solvent rich vapor to distillation in a separation zone to form a solvent rich stream and a benzoic acid rich stream;
    wherein said benzoic acid rich stream comprises from about 5 wt % to about 35 wt % benzoic acid; and
    (c) recycling at least 50 wt % of the solvent rich stream to an oxidation reactor in an aromatic oxidation process.

13. The process according to claim 12 wherein said benzoic acid bearing stream is a vapor stream produced in the oxidation of an aromatic compound.

14. The process according to claim 12 wherein at least 75 wt % of said benzoic acid rich stream is recycled to an oxidation reactor in an aromatic oxidation process.

15. The process according to claim 12 wherein said evaporator zone is operated between about 1 to about 10 atmospheres.

16. The process according to claim 12 wherein all of the solvent rich stream is recycled to an oxidation reactor process.

* * * * *